United States Patent
Charles

(10) Patent No.: US 7,684,998 B1
(45) Date of Patent: *Mar. 23, 2010

(54) METHOD TO PROVIDE EMERGENCY HEALTH CARE TO PATIENTS WITH INSURANCE

(76) Inventor: Ronald Alan Charles, 8906 Wallington Dr., Houston, TX (US) 77096

(*) Notice: Subject to any disclaimer, the term of this patent is extended or adjusted under 35 U.S.C. 154(b) by 1688 days.

This patent is subject to a terminal disclaimer.

(21) Appl. No.: 10/863,791

(22) Filed: Jun. 8, 2004

Related U.S. Application Data

(60) Provisional application No. 60/492,479, filed on Aug. 4, 2003.

(51) Int. Cl.
  *G06Q 10/00* (2006.01)
  *G06Q 50/00* (2006.01)
(52) U.S. Cl. .......................................... 705/2
(58) Field of Classification Search .................. 705/2–4
  See application file for complete search history.

(56) References Cited

U.S. PATENT DOCUMENTS

| | | | |
|---|---|---|---|
| 6,345,260 B1* | 2/2002 | Cummings et al. ............ | 705/8 |
| 2002/0010597 A1 | 1/2002 | Mayer et al. | |
| 2002/0019749 A1 | 2/2002 | Becker et al. | |
| 2002/0026328 A1 | 2/2002 | Westerkamp et al. | |
| 2002/0032580 A1* | 3/2002 | Hopkins ......................... | 705/2 |
| 2002/0042724 A1* | 4/2002 | Victor ............................ | 705/2 |
| 2002/0062224 A1 | 5/2002 | Thorsen et al. | |
| 2002/0103680 A1 | 8/2002 | Newman | |
| 2003/0050794 A1 | 3/2003 | Keck | |
| 2003/0208380 A1 | 11/2003 | Honeycutt | |
| 2004/0078220 A1 | 4/2004 | Jackson | |
| 2004/0220829 A1 | 11/2004 | Baharav et al. | |

* cited by examiner

*Primary Examiner*—Gerald J. O'Connor
*Assistant Examiner*—Sheetal R Rangrej
(74) *Attorney, Agent, or Firm*—Buskop Law Group, PC; Wendy Buskop

(57) ABSTRACT

The methods to provide emergency health care to patients with insurance entail creating a special care unit in a hospital and creating a contractual relationship between the special care unit and an association. The qualified patient is insured through the association and is provided with an indicator. An interface is provided for the qualified patient to request an actual time to be seen by the team; confirming the actual time; receiving the qualified patient with the indicator at the actual time, wherein the qualified patient is seen by the team in less processing time than the emergency department; evaluating the qualified patient within 30 minutes of the actual time to ascertain a medical problem; determining if the qualified patient stays in the special care unit or is to be transferred to the hospital's emergency department; treating the qualified patient based on the evaluation; and dispositioning the qualified patient.

11 Claims, 1 Drawing Sheet

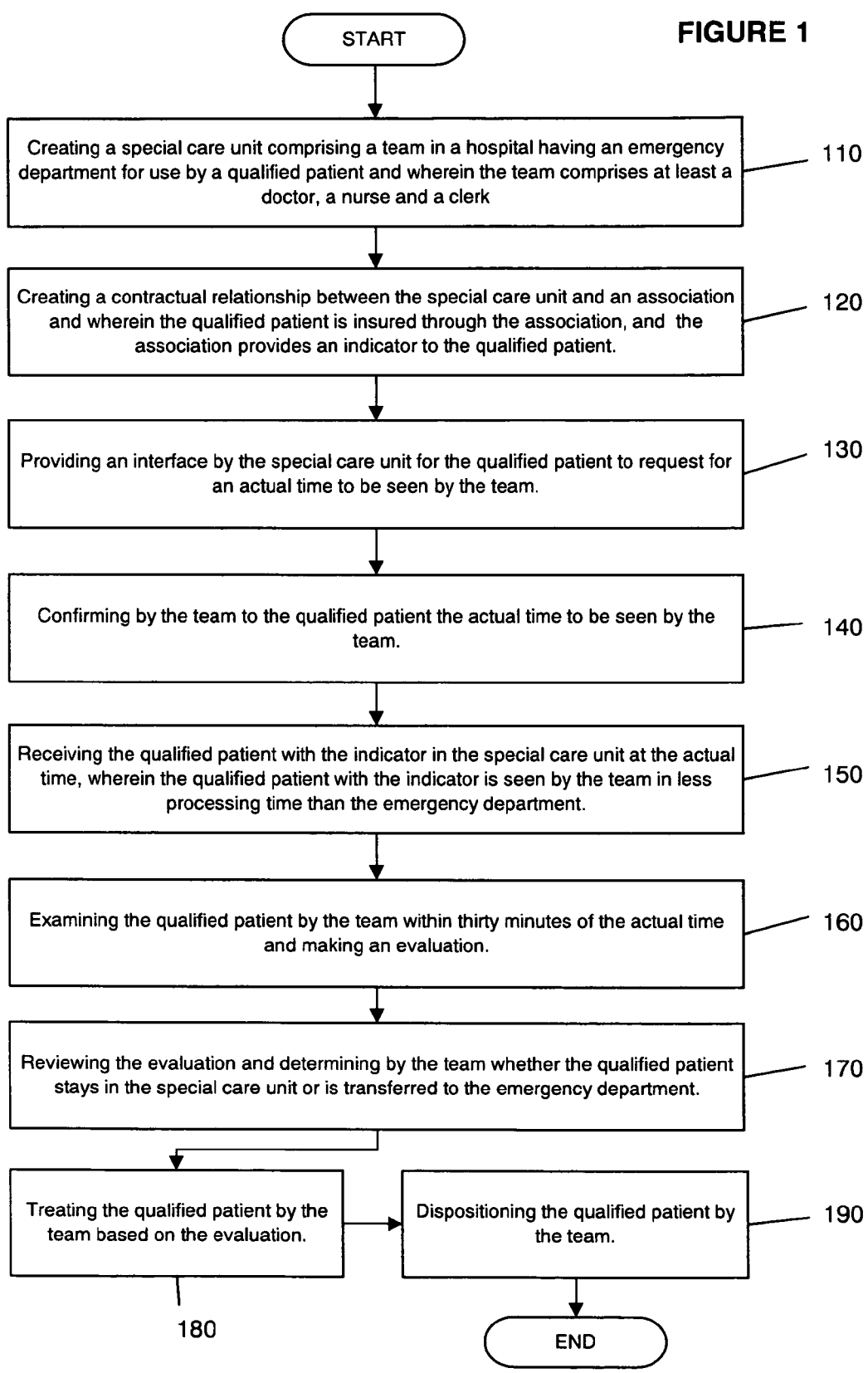

METHOD TO PROVIDE EMERGENCY HEALTH CARE TO PATIENTS WITH INSURANCE

The present application claims priority to U.S. Provisional Patent Application Ser. No. 60/492,479 filed on Aug. 4, 2003.

FIELD

The present embodiments relate to methods to provide emergency health care to patients with insurance.

While these methods have nearly universal application within varying departmental hospital environments, a number of features of the present embodiments are optimized for use within a hospital's Emergency Department facility.

BACKGROUND

The present embodiments relate generally to a process for managing health care and address many of the problems faced today by those involved with health care: payers, patients, and providers. The methods relate particularly to techniques for improving personalized care at hospitals that interface health plan associations who have decided to seek health care services from a doctor and/or some other type of health care provider. These calls are answered by nurses and/or other types of health care professionals, who use the proprietary information tools and processes of the network management system to help patients assess their health needs and then select appropriate care.

The United States ranks first in the world in per-capita health care expenditures. At a time when national health care costs continue to escalate at an alarming rate, managed-care companies and the government have been successful in holding down payments to hospitals; but too often the patient feels unattached from the process. This feeling often leads to a reluctance of patients to seek out the help they need.

Additionally, profit margins of hospitals are decreasing yearly. To survive financially, hospital administrators have been forced to develop novel means of ensuring that their hospital is properly compensated for all services rendered and that patients are treated in manner that encourages them to return to the hospital in times of need. Today, the provision of medical care or personal care for a patient in a hospital often assumes a subordinate role to the extensive amount of information that the hospital requires from the patient. Hospital administrators often need to maintain significant quantities of patient data consisting of information such as admissions, medical history, insurance, and billing. To meet the ever increasing financial demands of providing high quality health care to patient's proper reimbursement from insurance companies is absolutely essential. Complicating the problem is the unique, often hectic, nature of an Emergency Room.

Working under highly stressful conditions, emergency medical team members are routinely forced to forego personalized care in order to balance administrative tasks and treat multiple patients suffering from severe injuries. Often, patients arrive in an Emergency Room with reduced communicative abilities as to their identity, compounded with life threatening injuries that require immediate medical attention. An attending Physician may issue an array of orders ranging from X-rays, administration of medication, and laboratory assays; all of which must be tracked and recorded to insure proper billing and reimbursement. In these situations, it is unacceptable to interfere with the administration of care in order to obtain patient medical care, or resource utilization data. Often when there is interference with the administration of care the patient is ignored as a person and treated as a series of problems. This only adds to anxiety of the patient and increases their feeling of isolation towards the hospital.

A majority of patients initially come to a hospital through the Emergency Room. A patient will inevitably make a decision about using the hospital for future needs, as well as recommending the hospital to others, based on this initial visit and the treatment during that visit. For hospitals to remain viable and competitive, they must make an effort to personalize care in the Emergency Room in order to encourage patients to choose their hospital for future needs.

Furthermore, most patients with insurance obtain their insurance through a membership with an association. Associations can be any group of people from unions to employees of the same company. A need exists for hospitals to implement a marketing agreement with these types of associations. These associations can actively advise their members of the warm and responsive environment in the hospital and the customer friendly atmosphere in the area surrounding the Emergency Room. In return, the hospital can implement a program where a patient belonging to one of these associations can be identified as a qualified patient merely by their membership.

A qualified patient can be identified by uniform, known trademark, employee identification card, or some other means of identification that associates the patient as a member of one the associations. This type of relationship would create revenue for the hospital by increasing the number of people who use the facility and would personalize the experience for the patient.

A need exists for a method to provide emergency health care to patients with insurance. This method would allow hospital administrators to optimize utilization of resources, including utilization of medical personnel, such as nurses, and other medical resources, such as beds, medications, and the like. The method will additionally provide the ability to track effectively the efficiency of patient care provision on a personalized level. This is the ultimate goal of the Emergency Room.

In a broader sense, this method would allow hospital administrators to monitor the cumulative activity of a given department over a time period and assess staff and administrative efficiency as needed to determine if personalized care is being given and if those patients are returning to the hospital for their future needs.

An even more pressing need exists for patients with insurance to get the care they deserve and need and that is covered by an insurance policy that pays the costs of the medical care.

SUMMARY

The method to provide emergency health care to patients with insurance entail providing an interface for a qualified patient to request an actual time to be seen by a team member of a special care unit in a hospital having an emergency department while additionally providing a confirmation to the qualified patient of the request for the actual time to be seen by the team member. The methods continue by evaluating the qualified patient by the team member at the special care unit within 30 minutes of the actual time to ascertain the medical problem; determine if the qualified patient stays in the special care unit or is transferred to the hospital's emergency department; treating the qualified patient based on the evaluation of the medical problem; and dispositioning the qualified patient.

BRIEF DESCRIPTION OF THE DRAWINGS

The present embodiments will be explained in greater detail with reference to the appended Figures, in which:

FIG. 1 is a schematic diagram of the steps of an embodiment of a method to provide emergency health care to patients with insurance.

The present embodiments are detailed below with reference to the listed Figures.

DETAILED DESCRIPTION OF THE PREFERRED EMBODIMENTS

Before explaining the present embodiments in detail, it is to be understood that the embodiments are not limited to the particular embodiments herein and can be practiced or carried out in various ways.

The embodied methods for providing emergency health care to patients with insurance are cost effective, save lives, and increases productivity of health care providers. The methods promote improved health care. These novel methods are designed to get injured workers back to work quicker, which, in turn, provides an overall stimulus to the economy.

With reference to the Figures, FIG. 1 is a schematic diagram of the steps of an embodied method. The method begins by creating a team for a special care unit (110). The team is made optimally from at least three members, a nurse, a physician, and a clerical staff member. This team such as this for the special care unit is trained with a program that focuses on customer service and care. The special care unit team members have special training, reading materials, tests and evaluations to insure a high level of customer service in the special care unit. The method anticipates that periodic review of the level of care can occur with comment cards and spot inspections.

The method continues by implementing a contractual agreement between the association, hospital, and the management group of the special care units (120). Under the agreement, the association and the management group work together to market the special care units to potential qualified patients. The association and the management group notify the potential qualified patients of the locations of the special care units; the hours of service available for the special care units; the phone numbers of the special care units or a scheduling service; the web site address of the special care units; an information center to answers questions about the special care units; and other pertinent information needed to have the potential qualified patients easily access the special care units.

The method contemplates that the association and the management group accomplish the task of marketing the special care units by utilizing newsletters, meetings, e-mails, direct mailings, advertisings, and combinations thereof. Examples of advertising include stickers, magnets, promotional items, and other similar tokens used to market the special care units. The associations advise their members of them on a regular basis, but at least monthly as a minimum.

The association and the indicator are registered with the special care unit to identify other members as qualified patients. The association attempts to provide appropriate insurance information to the special care unit so that the care of the qualified patient can be expedited. The association informs the qualified patient that they should mention the special care unit when they are present in the emergency department triage for treatment.

Next, as shown in FIG. 1, an interface is provided for a qualified patient to request an actual time to be seen by a team member within the special care unit (130).

The method operates for individuals who are referred to hereafter as qualified patients. Qualified patients are individuals whom have contracted for specialized care from a qualified team of health professionals through an organization. Examples of these types of organizations include unions, employers, credit unions, and organizations, such as AAA or AARP. An organization can be an association of numerous members from a defined region. The method contemplates that the organization incorporates a group of people associated with one another through a health plan.

The qualified patient is a person that can be identified and educated about the special care units. The special care unit preferably is situated in a space near or close to the emergency department of a hospital. In the special care unit, the qualified patient typically has insurance already preprogrammed into a database that enables the qualified patient to obtain the care from the special care unit.

A qualified patient, as an individual, can be a union member, a police officer, a hospitality industry member, a hospital employee, an emergency medical services member, a governmental worker, or any other worker identified by uniform. The qualified patient can belong to an association, such as an union or a corporation that has a visually identifiably and unique identification mark, such as a sticker with an employee logo, an employee badge, a distinct trademark, a uniform, or a corporation issued smart card.

Family members with insurance are also be qualified patients under this method. A family member is a spouse, dependent, or any other specially designated persons of the primary insured. Specially designated persons can include grandparents, life partners, foster children, dependent aunts, dependent uncles, and siblings.

The qualified patient communicates with the team members using an on-line query service or a telecommunication device. Usable devices include cell phones, satellite phones, or landline phones. The qualified patient can also contact the team members using a pager, a PDA, or a phone and PDA combination. Other methods include access through an internet website or by mail service. Any one or combination of these manners to communicate can be utilized.

Returning to FIG. 1, the qualified patient requests an actual time to be seen by a team member within a special care unit in a hospital having an emergency room or emergency department (130). For example, the actual time requested by the qualified patient is a defined specific time, such as 9:15 am. The qualified patient can request any hour of the day that is not already requested by another qualified patient and during that the special care unit is open. Typically, the special care unit can be open for 10 to 12 hour shifts and possibly for 24/7 shifts (24 hours, 7 days a week). The team member is preferably seen within a 30 minute window around the actual specific time by the qualified patient. If the qualified patient misses this preferred 30 minute window, the methods may include an optional increase in the amount of the co-pay by an amount of a penalty. For example, a penalty of up to $40 can be assessed against a late arriving or non-arriving patient.

The method contemplates that the team member is a person qualified to handle the needs of the qualified patient. Preferably, the team member is a nurse, nurse practitioner, physician, physician assistant, and combinations thereof. Additionally, a team member can include a clerical member, trained to handle accounting, billing or other clerical tasks, a nurse, a nurse practitioner, or other such person in a position to be of qualified assistance.

Continuing with FIG. 1, the next step in the embodied methods is providing a confirmation to the qualified patient of the request for the actual time to be seen by the team member (140). The confirmation of the request for the actual time to be seen by the team member can be completed by a verbal confirmation, an e-mail confirmation, a confirmation by pager, a confirmation by written letter (that is faxed), and combinations thereof. Any of the communication methods used by the qualified patient to communicate with the team member can be used by the team member to confirm the request for the actual scheduled time.

Next, the qualified patient with the indicator is received in the special care unit at the actual time (150). A qualified patient with an indicator is seen by the team in less processing time than what can normally be the processing time if the qualified patient were to enter through the emergency department.

The process continues by the qualified patient team within thirty minutes of the actual time to ascertain the medical problem and make an evaluation (160). The evaluation involves a physical examination, taking of the patient's history and ordering any necessary tests.

The method contemplates that bedside registration for the qualified patient is possible when the services are available.

The method continues by the team members reviewing the qualified patient and determining whether the patient stays in the special care unit or is transferred to the emergency department (170). If the qualified patient stays in the special care unit or is transferred to the hospital's emergency room or department the treatment is based on the evaluation of the medical problem made by the special team unit (180). The team member can contact the emergency department and advise of the need to transfer the patient to the emergency department. The patient can then be physically moved to the higher level of care area in the emergency department from the special team unit.

If transfer is not required, then treatment of the qualified patient can include writing a prescription and contacting a contracted pharmacy for expedited filling of the prescription for patient pickup.

Treatment for the qualified patient may also include ordering various tests, such as a blood tests, urine tests, radiological tests, cardiac tests, stool tests, and combinations thereof. Any test and treating procedures normal to emergency rooms can be used with the method.

The contracted pharmacy can be a 24 hour pharmacy that is near the special care unit. This pharmacy can have a separate contract with trained pharmacists who are adept to quickly filling prescriptions and have the filled prescriptions available to the qualified patient when they arrive at the pharmacy. The contracted pharmacy can have not only increased volume, but increase revenue due to this specially contracted service. The expedited filling of the prescription for patient pickup can be completed by written, electronic, or verbal communication.

One of the goals of this method is to provide good customer service from valet or reserved parking to personalized care in order to expedite pharmacy prescription pick-up.

Returning to FIG. 1, the final step is dispositioning the qualified patient (190). Dispositioning means discharging from the hospital, transferring the patient to another area of the hospital, transferring the patient to a clinic, a nursing home, an assisted-care unit, or to another facility for testing. After the patient is dispositioned, the qualified patient can arrange a follow-up appointment with another physician on their insurance plan in the hospital system, in the same manner as the original appointment was made.

If necessary, and if permitted by the qualified patient, the team member provides the qualified patient's employer or a second physician with treatment information.

The method contemplates that the physician or other team member can use a cell phone with camera system, such as the ones made by Sony or Ericsson, or a digital camera, to photograph and e-mail the patient conditions and situation to a private physician, such as showing the physician abscess.

The team members can use PDA or personal digital assistants with wireless connectivity in order to access the Internet to register a patient, and enter information while in the examining room directly to the medical records database interfaced and accessed by the team.

Tablet PC's can be used by the team members to draw important information about the condition of the patient. Other types of usable electronic devices include voice recognition, special phone services or template medical record systems.

The team member is part of a qualified team. The qualified team is developed for use in a designated hospital, especially hospitals with emergency rooms. The team operates in an area near or adjacent to the emergency room; these areas are known as "Special Care Units". The "Special Care Units" are designed to allow the qualified team to handle the qualified patients without the need for minimal emergency room equipment. In a preferred embodiment, the special care unit comprises at least one examination room, at least one computer, and at least one work area, however special care units can operate with just one examination room. Software on the computer allows for scheduling of qualified patients, production of reports for patient charts, and an interface with the hospital and other medical databases to download patient histories. The scheduling software provides an indication of the availability of when a patient can be seen by the team.

The methods contemplate that all information on the patient, the evaluation, and the diagnosis can be completed by using electronic charting, electronic time slotting, and electronic reporting. These types of electronic programs are widely known throughout the medical industry. An example of such as electronic system is the T-System, which is a form of a template medical records system available for use on a laptop or tablet or PDA.

The examining rooms in the "Special Care Units" are typical rooms, with an otoscope, opthalmoscope, thermometer, instruments to take blood pressure, gynecologic equipment, examining tables, chairs, sinks, other tables, scalpels, and medical supplies, such as needles, gauze, and suture material. The methods contemplate that these "Special Care Units" can have the routine equipment and supplies usually stocked in a typical medical care room. The examining rooms also include certain medications including pain medications and antiseptics for cleaning wounds. The work area provides an area where paperwork can be handled and where the computer and an Internet connection can be located.

The qualified team typically has at least three members: a clerk, a nurse, and a physician. The team can have more than three members, such as two or more doctors and nurses and/or more clerks depending on the need at a given hospital.

While these embodiments have been described with emphasis on the preferred embodiments, it should be understood that within the scope of the appended claims the embodiments might be practiced other than as specifically described herein.

What is claimed is:

1. A computer implemented method to provide emergency health care to patients with insurance comprising the steps of
   a. establishing a special care unit comprising at least one examination room, at least one interface on at least one computer, and at least one work area, and forming a team within the special care unit, in a hospital having an emergency department for use by a plurality of qualified patients or a plurality of family members of a qualified patients and wherein the team has a doctor and at least one member of the group comprising at least one nurse, at least one clerk or combinations thereof; and wherein the special care unit provides to qualified patients or to the family members of the qualified patients services including: providing scheduling services at least for an actual time for an examination, providing an examination, providing at least one test with results enabling the doctor to provide an evaluation, providing treatment based on the evaluation; and providing dispositioning of the qualified patient or the family member of the qualified patients,
   b. verifying a person's insurance through a association, and for a fee providing an indicator to the person to identify the person as a qualified patient or as a family member of the qualified patients; wherein the indicator provided by the association is for enabling the qualified patient or the family member of the qualified patients to have emergency healthcare within thirty minutes of the actual time registering the indicator with the special care unit; wherein the indicator is selected form the group comprising a uniform, an association identification badge, an association trademark, a sticker with a unique identification mark, a corporation issued smart card, or combinations thereof; and
   wherein the interface enables the qualified patient or the family member of the qualified patients to request the actual time to be seen by the special care unit and the interface includes computer instructions executable on a computer for scheduling the qualified patient or the family member of the qualified patients for the actual time to be seen by the team and wherein the computer instructions are in a data storage on the computer, and further wherein the computer instructions in the data storage enable production of reports for patient charts and enable communication with medical databases for downloading patient histories;
   c. confirming by a computer by the team to the qualified patient or to the family member of the qualified patients the actual time to be seen by the team; by providing a confirmation that is a verbal confirmation, an email confirmation, a confirmation by pager, a or combinations thereof;
   d. receiving the qualified patient or the family member of the qualified patients with the indicator in the special care unit near the actual time, wherein the qualified patient or the family member of the qualified patients with the indicator is seen by the team;
   e. examining the qualified patient or the family member of the qualified patients by the team;
   f. making an evaluation to either keep the qualified patient or the family member of the qualified patients in the special care unit or to transfer the qualified patient or the family member of the qualified patients to a higher level of care area in the emergency department;
   g. in the special care unit, if no transfer to the higher level of care area is made, then the qualified patient or the family member of the qualified patients is treated by the team based on the evaluation; and
   h. dispositioning the qualified patient or the family member of the qualified patients by the team.

2. The computer implemented method of claim 1, wherein the qualified patient is a member selected from the group consisting of a union member, police officer, hospitality industry member, teacher, hospital employee, emergency medical services member, a governmental worker, and combinations thereof.

3. The computer implemented method of claim 1, wherein the family member is a member selected from the group consisting of a spouse, at least one dependent, a specially designated person, and combinations thereof.

4. The computer implemented method of claim 1, wherein the association comprises at least one of consisting of a union, government agency, emergency medical service group, police officer group, fire fighter group, employee group, human resource department of a company, teacher association, a retired person association, and combinations thereof.

5. The computer implemented method of claim 1, wherein the team further comprises at least a second clerk, at least a second nurse, at least one nurse practitioner, at least a second doctor, at least one physician's assistant, and combinations thereof.

6. The computer implemented method of claim 1, wherein the step of providing the interface uses a member selected from the group consisting of a website, telephone service, telephone operator, pager, letter, and combinations thereof.

7. The computer implemented method of claim 1, wherein after making the evaluation the doctor writes a prescription and a pharmacy is contacted by the team for expedited filling of the prescription in less than thirty minutes of the actual time, for the qualified patient or the family member of the qualified to pickup the prescription.

8. The computer implemented method of claim 1, wherein the test is selected from the group consisting of a blood test, urine test, radiological test, cardiac test, stool tests, and combinations thereof.

9. The computer implemented method of claim 1, wherein the step of dispositioning the qualified patient or the family member of the qualified patient further comprises a step of arranging a follow-up appointment by the team.

10. The computer implemented method of claim 1, wherein after the step of dispositioning the qualified patient or the family member of the qualified patient, further comprising a step of providing the association with treatment information at the request of the qualified patient or the family member of the qualified patient, and wherein the treatment information is provided by the team.

11. The computer implemented method of claim 1, wherein after the step of dispositioning the qualified patient or the family member of the qualified patient further comprising a step of providing a second physician with treatment information at the request of the qualified patient or the family member of the qualified patient and wherein the treatment information is provided by the team.

* * * * *